(12) United States Patent  
Lall

(10) Patent No.: US 7,099,237 B2  
(45) Date of Patent: Aug. 29, 2006

(54) TIME KEEPING SYSTEM AND WATCH

(76) Inventor: Sardool Singh Lall, 99 Worple Way, Harrow (GB) HA2 9SW ( * ) Notice: Subject to any disclaimer, the term of this patent is extended or adjusted under 35 U.S.C. 154(b) by 69 days.

(21) Appl. No.: 10/380,674

(22) PCT Filed: Sep. 19, 2001

(86) PCT No.: PCT/GB01/04192

§ 371 (c)(1),  
(2), (4) Date: Mar. 18, 2003

(87) PCT Pub. No.: WO02/25383

PCT Pub. Date: Mar. 28, 2002

(65) Prior Publication Data

US 2005/0099894 A1    May 12, 2005

(51) Int. Cl.  
*G04B 47/00* (2006.01)  
*G04B 19/00* (2006.01)  
*A61B 5/04* (2006.01)

(52) U.S. Cl. .................. 368/10; 368/223; 600/509; 600/523

(58) Field of Classification Search ............... 368/100, 368/10, 82, 223, 278; 600/509, 523  
See application file for complete search history.

(56) References Cited

U.S. PATENT DOCUMENTS

| 3,216,261 | A | * | 11/1965 | Brown ..................... 600/519 |
| 4,221,223 | A | * | 9/1980 | Linden ..................... 600/519 |
| 4,406,290 | A | * | 9/1983 | Walbeoffe-Wilson et al. ..................... 600/502 |
| 4,489,731 | A | * | 12/1984 | Baumberg ..................... 600/503 |
| 4,898,179 | A | * | 2/1990 | Sirota ..................... 600/483 |
| 5,335,664 | A | * | 8/1994 | Nagashima ..................... 600/508 |

* cited by examiner

*Primary Examiner*—Vit W. Miska

(57) ABSTRACT

The present invention concerns the field of watches and time pieces. There is disclosed a mechanism for a watch (10) configured so that heartbeats act as the trigger that initiates updating of a second unit display. There is also described a mechanism for a watch adapted so that a heartbeat acts as a trigger to increment the time display (21). Furthermore there is disclosed a watch which is associated with a heartbeat sensor (30), the watch being adapted to periodically update a time display in response to heartbeats detected by the sensor, whereby the time display is updated every time a heartbeat is sensed.

4 Claims, 1 Drawing Sheet

TIME KEEPING SYSTEM AND WATCH

This invention relates to systems for time keeping, and in particular relates to a mechanism in which the seconds display is updated in response to heartbeats of a person.

Analogue watches typically display time by means of a minute hand and an hour hand. Commonly analogue watches are also provided with a second hand. Digital watches display hours, minutes and seconds in terms of Arabic numerals.

Conventionally the seconds display, on a watch that is used to indicate the time of day, has a time increment between updating the seconds display that remains constant. Commonly the seconds display is updated every second, so that sixty updates occur every minute.

In addition to displaying the seconds unit, the seconds display (whether it is a moving hand or a changing numeral) visibly portrays the passage of time.

The present inventor has realised that it would be novel and desirable to portray the passing of time as heartbeats, which is not possible by means of a conventional watch.

It is known to provide watches which have a heart rate monitoring mode. These are typically provided with a chest strap for sensing heartbeats. The strap is provided with a transponder which communicates with a receiver in the wrist watch. The watch is provided with a processor for calculating heart rate, and display the heart rate. These watches are useful for cardiovascular fitness training and are widely used. Watches such as these are manufactured by several companies, such as POLAR ELECTRO OY. Other heart rate monitoring watches are available. For example Casio produce a watch having a finger pulse sensor built into the face, which allows pulse to be sensed by pressing of a finger onto the watch face. The watch display then calculates and indicates a heart rate. However, although a pulse rate may be given, and indeed a visual indication of each heartbeat displayed, the time display is an entirely separate feature, which is updated periodically but independently of the heartbeats of the person wearing the watch.

The present invention seeks, inter alia, to provide a watch in which a time display is updated in response to heartbeats. There is also provided a mechanism for a watch in which a heartbeat acts as the trigger to increment the time display.

According to one aspect of the present invention there is provided a mechanism for a watch wherein a heartbeat acts as the trigger that initiates updating of the seconds unit display.

According to another aspect of the invention, there is provided a watch which is associated with a heart beat sensor, the watch being adapted to periodically update a time display in response to heartbeats detected by the sensor, whereby the time display is updated every time a heartbeat is sensed.

According to another aspect of the invention there is provided a watch provided with a display unit comprising indicators of hours, minutes and seconds units, the watch comprising a device for keeping track of time, which device is periodically read by the display unit so that the displayed time corresponds with that maintained by the time tracking device, which watch is associated with a heartbeat sensor for sensing heartbeats of a person, wherein the heartbeat sensor is in data communication with the display unit, and wherein updating of the display is triggered in response to heartbeat signals communicated by the heartbeat sensor.

The watch may be digital or analogue so that the updating move the seconds hand or increments seconds numerals on the display.

Although a preferred embodiment relates to a wrist watch, "watch" is intended to have a broad meaning, including clocks and other timepieces.

The heartbeat sensor preferably senses the heartbeat of the wearer and is worn on the wearer. However the sensor may be worn by a person other than the wearer.

In another aspect of the invention the watch is provided with a dual mode operation capability, the first mode being a heartbeat triggered updating mode and the second mode being an automatic periodic updating mode.

In a preferred embodiment the sensor is integrated into the watch, and senses heartbeats of the wearer via the wrist.

However, currently reliable heartbeat sensor data may best be obtained by means of a sensor located in proximity with the chest of a user. Hence the heartbeat sensor may be carried by a chest strap.

A specific embodiment of the invention will now be described by way of example only and with reference to the accompanying schematic drawing.

Figure 1:
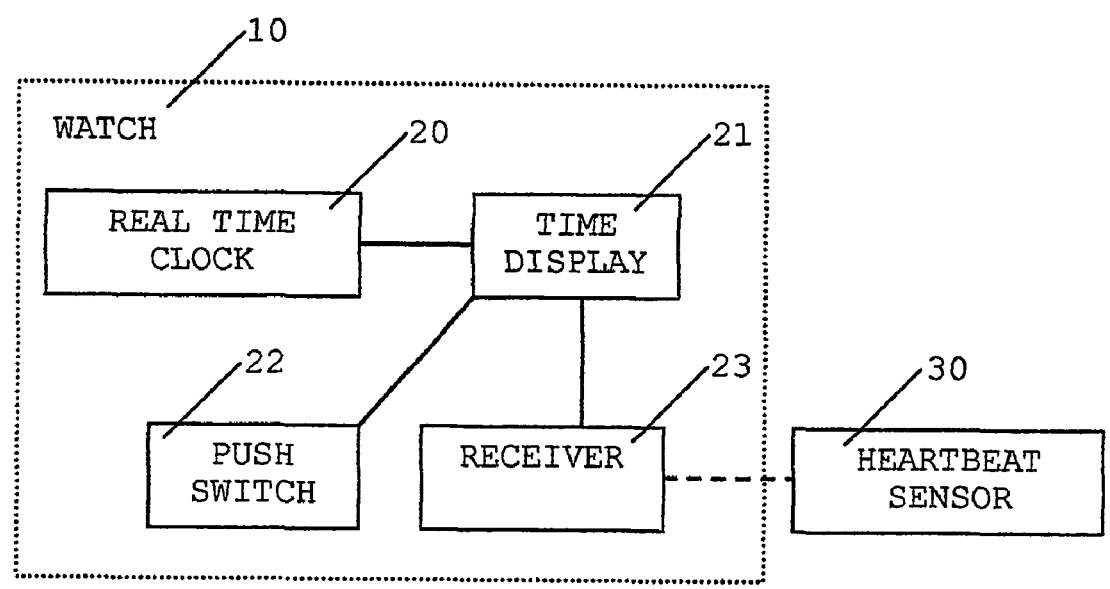
FIG. 1 is a schematic of the time keeping system and watch.

A time keeping device 20 forming part of a watch 10 is a real time clock formed as an integrated circuit. This clock maintains an internal record of the current real time. A time display unit 21 reads the time from the real time clock in response to an update trigger. In this way the displayed time is synchronised with the internal clock time. The time display unit only reads the real time clock and updates in response to an update trigger signal.

A heartbeat sensor 30 is a chest strap based unit, as known in the art of heart rate monitors. Each time a beat of the wearer's heart is sensed the sensor uses radio communication to transmit a signal to a receiver 23 in the watch.

The receiver sends a trigger signal to display unit. The display unit then reads the real time clock and updates the displayed time.

It will be evident that if the heart of the person wearing the sensor beats 60 times in one minute, then the display will be updated 60 times in that minute. However, if the heart rate is lower, say the heart beats 30 times in one minute, then the display would only be updated 30 times in that minute. Conversely, if the heart rate is higher, say the heart beats 120 times in one minute, then the display would be updated 120 times in that minute.

The watch of this embodiment is switchable between two modes, one in which the display is updated in response to heartbeats, as described above. In the other (standard) mode the display is updated in response to periodic automatic triggers sent by the real time clock, typically every second.

Switching standard mode or heartbeat mode is effected by manual depression of the push switch 22. Hence, in standard mode the display unit only carries out update operations at time period intervals of one second. In Heartbeat mode the display unit carries out a display update operation each time it receives a heartbeat signal from the heartbeat sensor.

What is claimed is:

1. A mechanism for a watch at least a seconds unit display for displaying at least seconds unit of time, the mechanism comprising means responsive to heartbeats to trigger initiating of the updating of the time displayed on the seconds unit display.

2. A mechanism for a watch with a time display comprising means responsive to heartbeats to trigger incrementing of the time displayed on the time display.

3. A watch having a time display for displaying time, the watch associated with a heartbeat sensor and having means adapted to periodically update the display in response to heartbeats detected by the sensor, whereby the time display is updated every time a heartbeat is sensed.

4. A watch provided with a display unit comprising indicators of hours, minutes and seconds units, the watch comprising a device for keeping track of time, which device is periodically read by the display unit so that the displayed time corresponds with that maintained by the time tracking device, which watch is associated with a heartbeat sensor for sensing heartbeats of a person, wherein the heartbeat sensor is in data communication with the display unit, and wherein updating of the display of time is triggered in response to heartbeat signals communicated by the heartbeat sensor.

* * * * *